(12) United States Patent
Oishi et al.

(10) Patent No.: US 9,594,302 B2
(45) Date of Patent: Mar. 14, 2017

(54) COMPOUND AND PHOTOSENSITIVE RESIN COMPOSITION

(71) Applicant: ADEKA CORPORATION, Tokyo (JP)

(72) Inventors: Takeo Oishi, Tokyo (JP); Koichi Kimijima, Tokyo (JP); Nobuhide Tominaga, Tokyo (JP); Hirokatsu Shinano, Tokyo (JP); Daisuke Sawamoto, Tokyo (JP); Kiyoshi Murata, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/381,772

(22) PCT Filed: Mar. 5, 2013

(86) PCT No.: PCT/JP2013/055968
§ 371 (c)(1),
(2) Date: Aug. 28, 2014

(87) PCT Pub. No.: WO2013/141014
PCT Pub. Date: Sep. 26, 2013

(65) Prior Publication Data
US 2015/0064623 A1 Mar. 5, 2015

(30) Foreign Application Priority Data

Mar. 22, 2012 (JP) ................................. 2012-065659
Sep. 4, 2012 (JP) ................................. 2012-194007

(51) Int. Cl.
| | | |
|---|---|---|
| G03F 7/004 | (2006.01) |
| C07D 209/88 | (2006.01) |
| C07D 211/70 | (2006.01) |
| C07D 233/06 | (2006.01) |
| C07D 241/06 | (2006.01) |
| C07D 403/12 | (2006.01) |
| C07D 401/12 | (2006.01) |
| C07D 209/86 | (2006.01) |
| G03F 7/038 | (2006.01) |

(52) U.S. Cl.
CPC ......... *G03F 7/0045* (2013.01); *C07D 209/86* (2013.01); *C07D 209/88* (2013.01); *C07D 211/70* (2013.01); *C07D 233/06* (2013.01); *C07D 241/06* (2013.01); *C07D 401/12* (2013.01); *C07D 403/12* (2013.01); *G03F 7/038* (2013.01)

(58) Field of Classification Search
CPC .. C07D 233/06; C07D 211/70; C07D 241/06; C07D 403/12; C07D 401/12; C07D 209/86; C07D 209/88
See application file for complete search history.

(56) References Cited

U.S. PATENT DOCUMENTS

| 8,088,836 | B2 | 1/2012 | Taguchi |
| 8,148,045 | B2 | 4/2012 | Murata et al. |
| 8,691,352 | B2 * | 4/2014 | Makino ........................ 428/1.31 |
| 8,940,464 | B2 | 1/2015 | Matsumoto |
| 2006/0211785 | A1 | 9/2006 | Aoai |
| 2009/0087759 | A1 | 4/2009 | Matsumoto |
| 2009/0246651 | A1 * | 10/2009 | Fujimori et al. .................. 430/7 |
| 2009/0292039 | A1 | 11/2009 | Sawamoto et al. |
| 2010/0044817 | A1 * | 2/2010 | Takakuwa et al. ............ 257/432 |
| 2010/0136491 | A1 * | 6/2010 | Matsumoto et al. ......... 430/325 |
| 2011/0129778 | A1 * | 6/2011 | Murata ................. C07C 251/66 430/281.1 |
| 2011/0233048 | A1 | 9/2011 | Kuramoto et al. |
| 2012/0176571 | A1 | 7/2012 | Makino |

FOREIGN PATENT DOCUMENTS

| CN | 101805281 | 8/2010 |
| CN | 102010475 | 4/2011 |

(Continued)

OTHER PUBLICATIONS

International Search Report, PCT/2013/055968, Jun. 4, 2013.
Extended European Search Report (EESR) Appln. No. 13764684.0; dated Nov. 27, 2015.

*Primary Examiner* — Martin Angebranndt
(74) *Attorney, Agent, or Firm* — Young & Thompson

(57) ABSTRACT

A novel compound having satisfactory sensitivity (base generating performance), a photosensitive resin composition containing the compound as a photo-initiator, and a cured product of the composition are provided. Specifically, a compound represented by general formula (1) (compound (1)), a photosensitive resin composition containing (A) a photo-initiator including at least one compound (1) and (B) a photosensitive resin are provided. Preferred are the compound (1) in which $R^1$ is an unsubstituted or substituted C6-C20 aromatic hydrocarbon group, the compound (1) in which at least one of $R^5$, $R^6$, $R^7$, $R^8$, $R^9$, $R^{10}$, and $R^{11}$ is nitro, and the compound (1) in which n is 0.

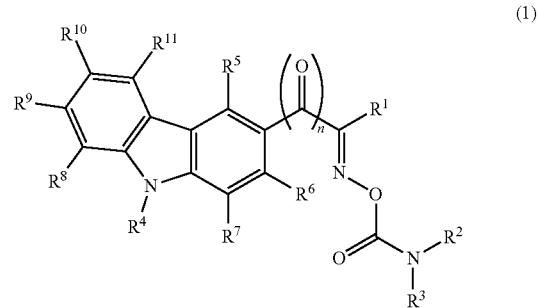

The symbols in general formula (1) are as defined in the description.

7 Claims, No Drawings

(56) References Cited

FOREIGN PATENT DOCUMENTS

| | | | |
|---|---|---|---|
| CN | 102086171 | | 6/2011 |
| EP | 1184382 | * | 3/2002 |
| EP | 2072500 A1 | | 6/2009 |
| EP | 2105443 | * | 9/2009 |
| JP | 2004-359639 | * | 12/2004 |
| JP | 2006-036750 | * | 2/2006 |
| JP | 2007-072034 | * | 3/2007 |
| JP | 2009-109921 | * | 5/2009 |
| JP | 2010-134453 | * | 6/2010 |
| JP | 2010-215575 | * | 9/2010 |
| KR | 20090008811 | * | 1/2009 |
| WO | 2007062963 A1 | | 6/2007 |
| WO | 2011030645 A1 | | 3/2011 |

* cited by examiner

COMPOUND AND PHOTOSENSITIVE RESIN COMPOSITION

TECHNICAL FIELD

This invention relates to a novel compound useful as a photo-base generator used in a photosensitive resin composition, a photosensitive resin composition containing a photosensitive resin and the compound, a cured product of the photosensitive resin composition.

BACKGROUND ART

A photosensitive resin composition generally comprises a photosensitive resin and a photo-initiator. Capable of polymerization by irradiation with energy rays (light) to cure or be developed, a photosensitive resin composition finds application in photocurable ink, a presensitized printing plate, a photoresist of various kinds, a photocuring adhesive, and the like.

Photo-initiators are classified into photo-radical generators, photo-acid generators, and photo-base generators according to the active species generated on irradiation with energy rays (light). A photo-radical generator is advantageous in that a high curing rate is achieved and that the active species does not remain after cure but is disadvantageous in that oxygen can cause hindrance to cure so that any means for blocking oxygen, such as an oxygen-barrier layer, should be provided in forming cured film. A photo-acid generator has an advantage of insusceptibility to inhibition by oxygen but is disadvantageous in that a residual acid as an active species can corrode a metal substrate or denature a cured resin. A photo-base generator is attracting attention because of its less likelihood of suffering from such problems as hindrance by oxygen to cure and corrosion by a residual active species. However, the problem with a photo-base generator is low sensitivity (low curing performance) as compared with a photo-acid generator. Photo-base generators are disclosed, e.g., in patent documents 1 to 3 below.

CITATION LIST

Patent Document

Patent document 1: EP 1032576
Patent document 2: US 2011/233048A
Patent document 3: WO 2010/064632

SUMMARY OF THE INVENTION

Problem to be Solved by the Invention

An object of the invention is to provide a novel compound having satisfactory sensitivity (base-generating performance), a photosensitive resin composition containing the compound as a photo-initiator, and a cured product of the composition.

Means for Solving the Problem

As a result of extensive investigations, the inventors have found that a compound having a specific structure exhibits high sensitivity, i.e., base-generating performance as a photo-initiator.

Based on the above finding, the invention provides a novel compound represented by general formula (I):

[Chemical Formula 1]

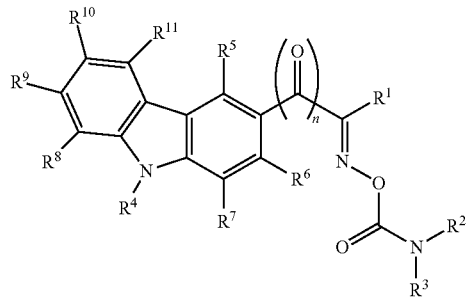

(1)

wherein $R^1$ represents an unsubstituted or substituted aliphatic hydrocarbon group having 1 to 20 carbon atoms or an unsubstituted or substituted aromatic hydrocarbon group having 6 to 20 carbon atoms, $R^2$ and $R^3$ each independently represent a hydrogen atom, an unsubstituted or substituted aliphatic hydrocarbon group having 1 to 20 carbon atoms or a phenyl group, or $R^2$ and $R^3$ are taken together to form a ring composed of a nitrogen atom and a carbon atom, $R^4$ represents an unsubstituted or substituted aliphatic hydrocarbon group having 1 to 20 carbon atoms, an unsubstituted or substituted aromatic hydrocarbon group having 6 to 20 carbon atoms, or an unsubstituted or substituted heterocyclic group having 2 to 20 carbon atoms, $R^5$, $R^6$, $R^7$, $R^8$, $R^9$, $R^{10}$, and $R^{11}$ each independently represent a hydrogen atom, a cyano group, a nitro group, —$OR^{12}$, —$COOR^{12}$, —CO—$R^{12}$, —$SR^{12}$, a halogen atom, an unsubstituted or substituted aliphatic hydrocarbon group having 1 to 20 carbon atoms, an unsubstituted or substituted aromatic hydrocarbon group having 6 to 20 carbon atoms, or an unsubstituted or substituted heterocyclic group having 2 to 20 carbon atoms;

$R^{12}$ represents an unsubstituted or substituted aliphatic hydrocarbon group having 1 to 20 carbon atoms, an unsubstituted or substituted aromatic hydrocarbon group having 6 to 20 carbon atoms, or an unsubstituted or substituted heterocyclic group having 2 to 20 carbon atoms, and n represents 0 or 1.

The invention also provides a photosensitive resin composition containing (A) a photo-initiator comprising at least one compound represented by general formula (I) and (B) a photosensitive resin.

The invention also provides a cured product obtained by irradiating the photosensitive resin composition with energy rays.

Effect of the Invention

When used as a photo-initiator, the novel compound of the invention is more effective in base generation than any conventionally known photo-base generators and therefore capable of causing a photosensitive resin to cure at a lower amount of exposure than required conventionally.

BEST MODE FOR CARRYING OUT THE INVENTION

The invention will be described in detail based on its preferred embodiments.

The novel compound of the invention is an oxime ester compound represented by general formula (1) shown above (hereinafter simply referred to as a compound(s) (1)). The compound (1) embraces geometric isomers based on the double bond of oxime, which are not distinguished from each other throughout the description of the invention. To put it another way, while the compounds (1), preferred compounds (1) hereinafter described, and illustrative examples of the compounds (1) shown later each represent one of the cis-trans isomers, the compounds of the invention are not limited to the isomeric structures described and may be the other isomers or a mixture of the two isomers.

In the cases where any group represented by $R^1$ to $R^{12}$ in general formula (1) is interrupted or substituted by a group containing a carbon atom, the number of the carbon atoms of the interrupting or substituent group is included in the respectively specified number of carbon atoms.

Examples of the unsubstituted C1-C20 aliphatic hydrocarbon group represented by $R^1$ in general formula (1) include methyl, ethyl, propyl, isopropyl, butyl, isobutyl, s-butyl, t-butyl, amyl, isoamyl, t-amyl, hexyl, heptyl, octyl, isooctyl, 2-ethylhexyl, t-octyl, nonyl, isononyl, decyl, isodecyl, undecyl, dodecyl, tetradecyl, hexadecyl, octadecyl, eicosyl, cyclopentyl, cyclohexyl, and cyclohexylmethyl. These aliphatic hydrocarbon groups maybe interrupted by —O—, —COO—, —OCO—, —CO—, —CS—, —S—, —SO—, —SO$_2$—, —NR—, —NR—CO—, —CO—NR—, —NR—COO—, —OCO—NR—, or —SiRR'—, provided that these interrupting divalent groups are not adjacent to each other.

R and R' each represent an unsubstituted aliphatic hydrocarbon group, examples of which include those listed above for the unsubstituted C1-C20 aliphatic hydrocarbon group represented by $R^1$.

Examples of the unsubstituted C6-C20 aromatic hydrocarbon group represented by $R^1$ in general formula (1) include phenyl, naphthyl, phenanthryl, pyrenyl, and biphenyl, each of which may be substituted with an aliphatic hydrocarbon group. The alkylene moiety of these aromatic hydrocarbon groups or the bond between $R^1$ and $R^1$ may be interrupted by —O—, —COO—, —OCO—, —CO—, —CS—, —S—, —SO—, —SO$_2$—, —NR—, —NR—CO—, —CO—NR—, —NR—COO—, —OCO—NR—, or —SiRR'—, provided that these interrupting divalent groups are not adjacent to each other.

Examples of the aliphatic hydrocarbon group include those listed above for the unsubstituted C1-C20 aliphatic hydrocarbon group represented by $R^1$.

R and R' each represent an unsubstituted aliphatic hydrocarbon group, examples of which include those listed above for the unsubstituted C1-C20 aliphatic hydrocarbon group represented by $R^1$.

Examples of the substituted C1-C20 aliphatic hydrocarbon group and the substituted C6-C20 aromatic hydrocarbon group as represented by $R^1$ include the above described examples of the corresponding unsubstituted groups the hydrogen atom of which is displaced by fluorine, chlorine, bromine, iodine, cyano, nitro, hydroxyl, thiol, —COOH, or —SO$_2$H.

Examples of the unsubstituted or substituted C1-C20 aliphatic hydrocarbon group as represented by $R^2$ and $R^3$ include those enumerated above for $R^1$. Examples of the ring composed of nitrogen and carbon atoms formed by $R^2$, $R^3$, and the nitrogen atom to which they are bonded include pyrrole, pyrrolidine, imidazole, imidazolidine, imidazoline, pyrazole, pyrazolidine, piperidine, and piperazine. The hydrogen atom of the ring may be replaced by fluorine, chlorine, bromine, iodine, cyano, nitro, hydroxyl, thiol, —COOH, —SO$_2$H, or an aliphatic hydrocarbon group.

Examples of the aliphatic hydrocarbon group include those described above for the unsubstituted C1-C20 aliphatic hydrocarbon group as $R^1$.

The unsubstituted or substituted C1-C20 aliphatic hydrocarbon group and the unsubstituted or substituted C6-C20 aromatic hydrocarbon group as represented by $R^4$ in general formula (1) include those described above for $R^1$, except that the bond between $R^4$ and the nitrogen atom is not interrupted.

Examples of the unsubstituted C2-C20 heterocyclic group as represented by $R^4$ include tetrahydrofuran, dioxoranyl, tetrahydropyranyl, morpholinofuran, thiophene, methylthiophene, hexylthiophene, benzothiophene, pyrrole, pyrrolidine, imidazole, imidazolidine, imidazoline, pyrazole, pyrazolidine, piperidine, and piperazine, each of which may be substituted with an aliphatic hydrocarbon group. The alkylene moiety of the heterocyclic group or the bond between the heterocyclic ring and an alkyl group may be interrupted by —O—, —COO—, —OCO—, —CO—, —CS—, —S—, —SO—, —SO$_2$—, —NR—, —NR—CO—, —CO—NR—, —NR—COO—, —OCO—NR—, or —SiRR'—, provided that these interrupting divalent groups are not adjacent to each other.

Examples of the aliphatic hydrocarbon group include those listed above for the unsubstituted C1-C20 aliphatic hydrocarbon group represented by $R^1$.

R and R' each represent an unsubstituted aliphatic hydrocarbon group, examples of which include those listed above for the unsubstituted C1-C20 aliphatic hydrocarbon group represented by $R^1$.

Examples of the substituted C2-C20 heterocyclic group as represented by $R^4$ include the above enumerated unsubstituted heterocyclic groups the hydrogen atom of which is replaced by fluorine, chlorine, bromine, iodine, cyano, nitro, hydroxyl, thiol, —COOH, or —SO$_2$H. In the cases where any group represented by $R^4$ is interrupted or substituted by a group containing a carbon atom, the number of the carbon atoms of the interrupting group or the substituent is included in the specified number of carbon atoms.

Examples of the unsubstituted or substituted C1-C20 aliphatic hydrocarbon group, unsubstituted or substituted C6-C20 aromatic hydrocarbon group, and unsubstituted or substituted C2-C20 heterocyclic group as represented by $R^5$, $R^6$, $R^7$, $R^8$, $R^9$, $R^{10}$, $R^{11}$, and $R^{12}$ include those enumerated above for $R^4$.

Of the novel compounds (1), those in which $R^2$ or $R^3$ is phenyl, those in which each of $R^2$ and $R^3$ is not hydrogen, those in which $R^2$ and $R^3$ are taken together to form a ring, those in which at least one of $R^5$, $R^6$, $R^7$, $R^8$, $R^9$, $R^{10}$, and $R^{11}$ is nitro, and those in which n is 0 are preferred in terms of UV sensitivity and curing performance when used in a curing composition. More preferred are compounds (1) in which $R^2$ and $R^3$ are taken together to form an imidazole or imidazoline ring, those in which $R^2$ and $R^3$ are taken together to form a piperidine ring, and those in which $R^{10}$ is nitro.

From the viewpoint of UV sensitivity, absorption of light of long wavelengths, and solubility in resins, compounds (1) in which $R^1$ is an unsubstituted or substituted C6-C20 aromatic hydrocarbon group are preferred, with those in which $R^1$ is phenyl or naphthyl each of which may be substituted by nitro, —COOH, or a C1-C20 aliphatic hydrocarbon group (which may be interrupted by —O—, —COO—, —OCO—, or —CO—) being more preferred.

From the viewpoint of UV sensitivity, absorption of light of long wavelengths, and solubility in resins, also preferred are compounds (1) in which at least one of $R^5$, $R^6$, $R^7$, $R^8$, $R^9$, $R^{10}$, and $R^{11}$ is nitro, cyano, hydroxyl, carboxyl, or thiol, with those in which at least one $R^5$ to $R^{11}$ is nitro being more preferred, and those in which $R^{10}$ is nitro being particularly preferred.

From the viewpoint of UV sensitivity and solubility in resins, also preferred are compounds (1) in which $R^4$ is an unsubstituted or substituted C1-C20 aliphatic hydrocarbon group (which may be interrupted by —O—, —COO—, —OCO—, or —CO—), phenyl, or naphthyl, with those in which $R^4$ is an unsubstituted C1-C10 aliphatic hydrocarbon group being more preferred.

In terms of UV sensitivity, absorption of light of long wavelengths, and solubility in resins, also preferred are compounds (1) in which at least one of $R^5$, $R^6$, $R^7$, $R^8$, $R^9$, $R^{10}$, and $R^{11}$ is —CO—$R^{12}$, with those in which R″ is —CO—$R^{12}$ being more preferred, and those in which $R^{12}$ is halogen-substituted phenyl being even more preferred.

Specific examples of the novel compound (1), compound Nos. 1 through 43, are shown below for illustrative purposes only but not for limitation.

[Chemical Formula 2]

No. 1

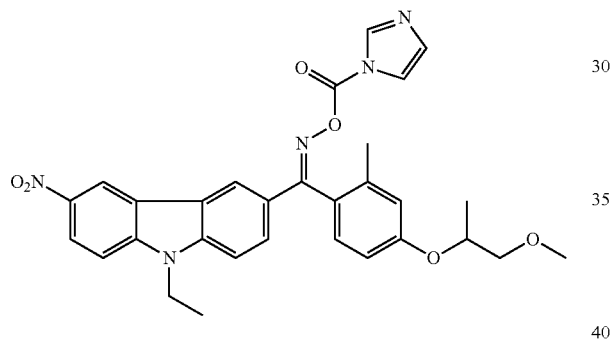

No. 2

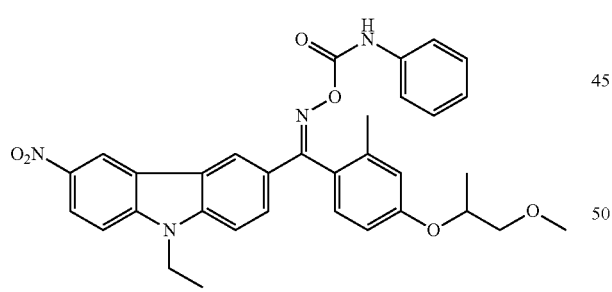

No. 3

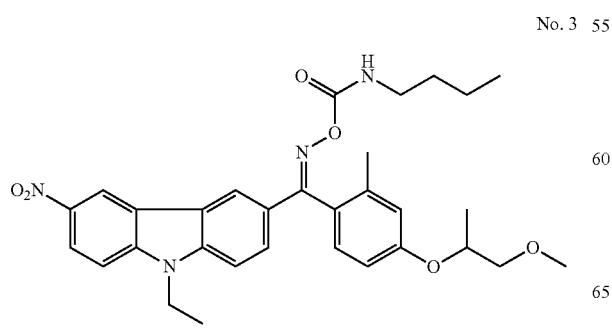

-continued

No. 4

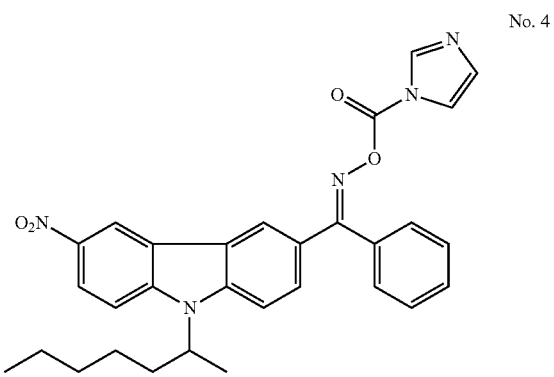

No. 5

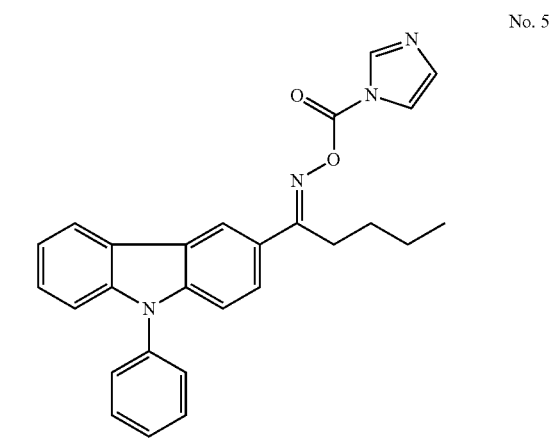

No. 6

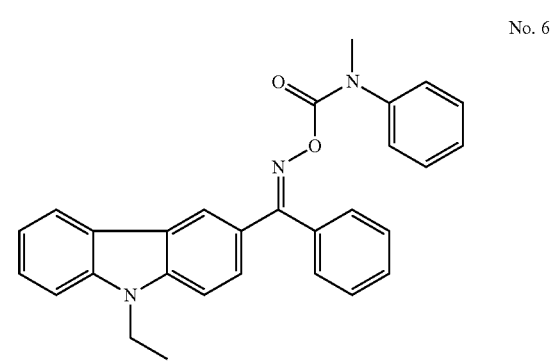

No. 7

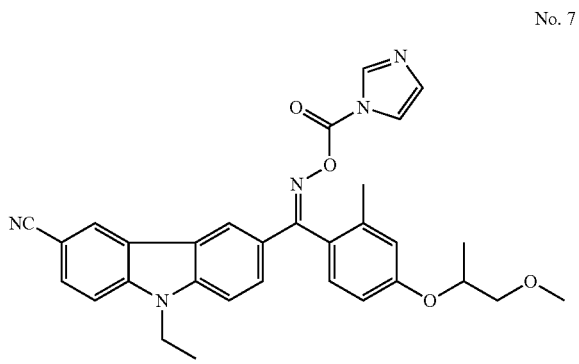

[Chemical Formula 3]

[Chemical Formula 4]
No. 17
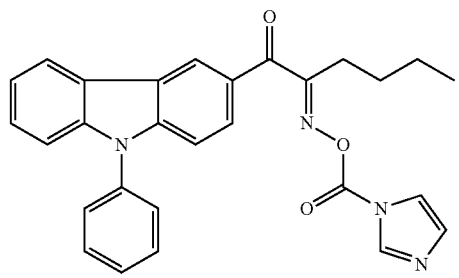
No. 18
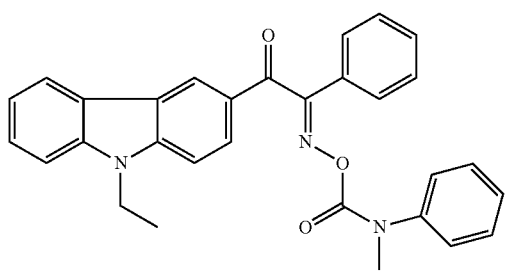
No. 19
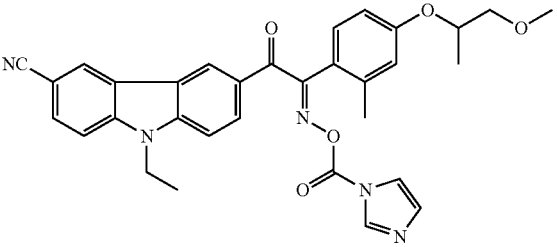
No. 20
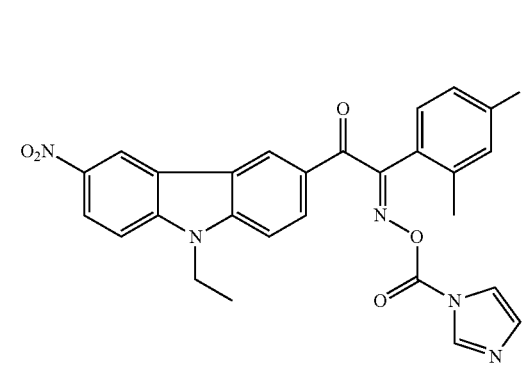
No. 21
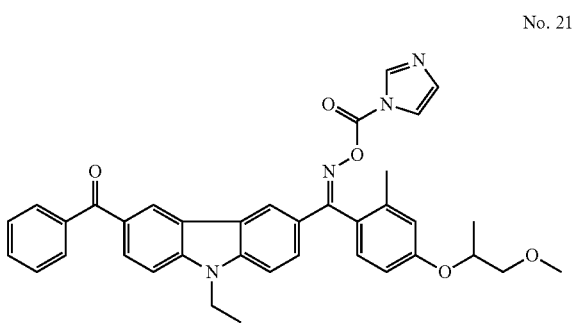
[Chemical Formula 5]
No. 22
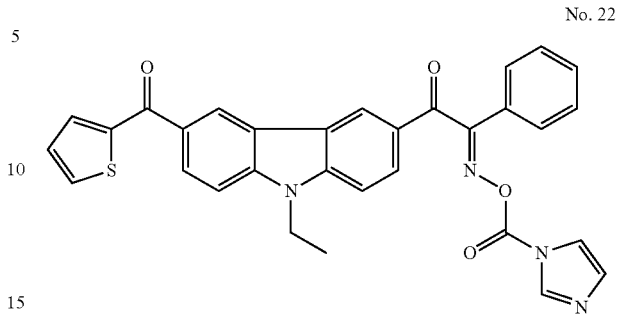
No. 23
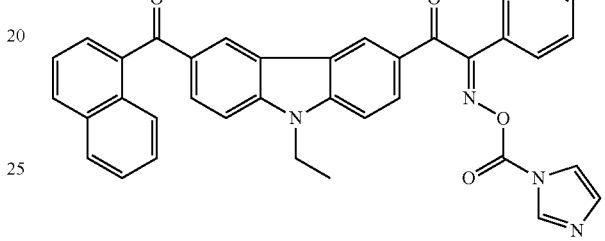
No. 24
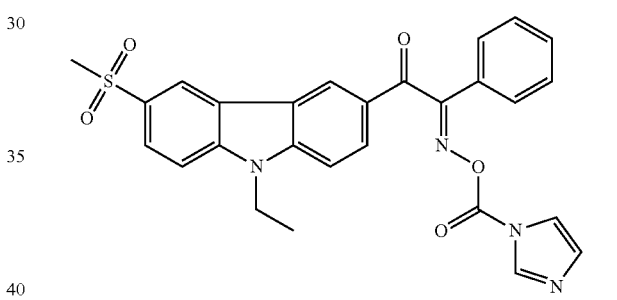
No. 25
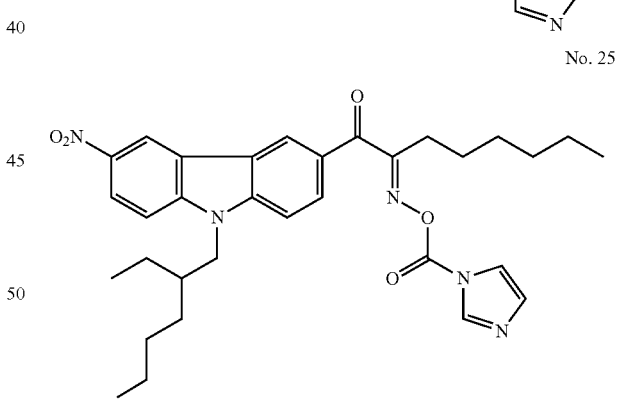
No. 26
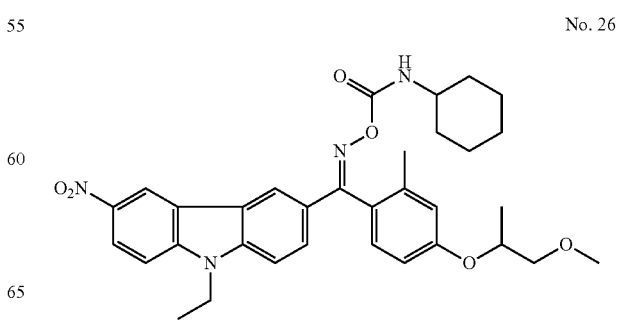

-continued
No. 27
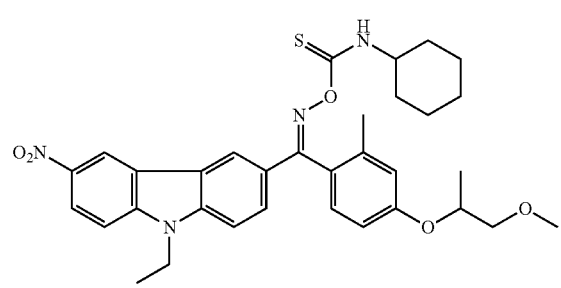
No. 28
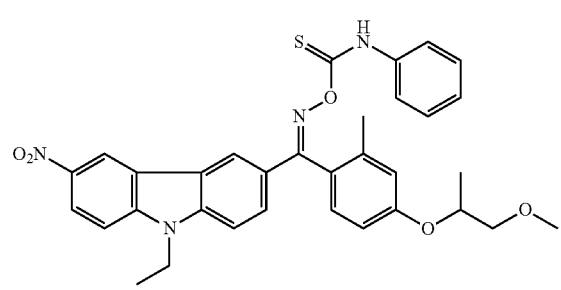
No. 29
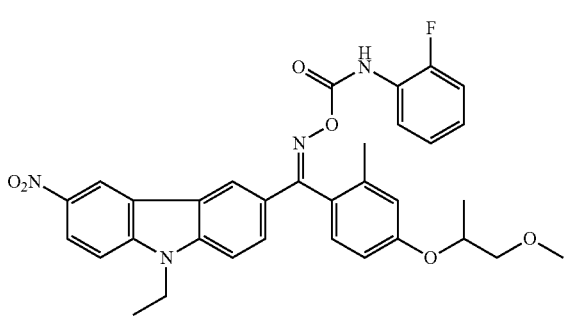
[Chemical Formula 6]
No. 30
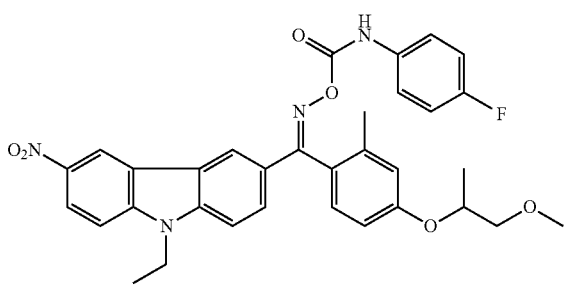
No. 31
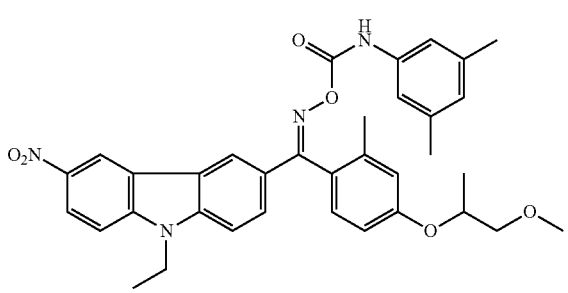
-continued
No. 32
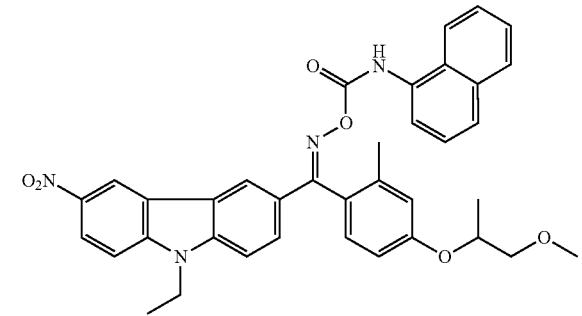
No. 33
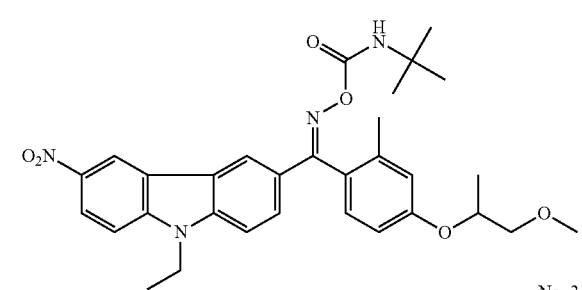
No. 34
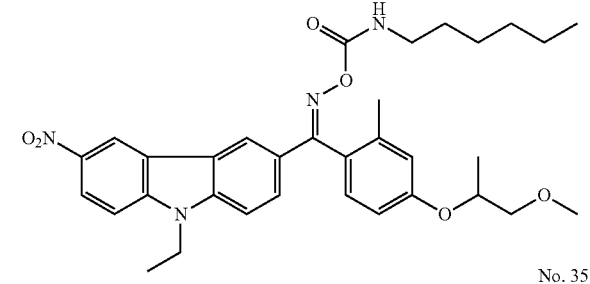
No. 35
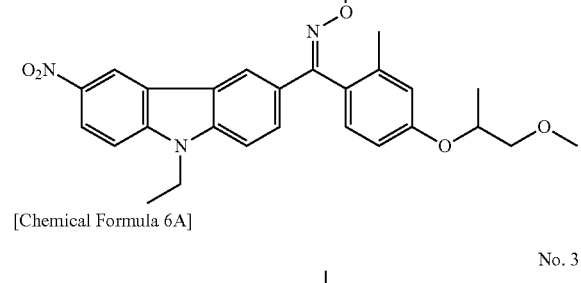
[Chemical Formula 6A]
No. 36
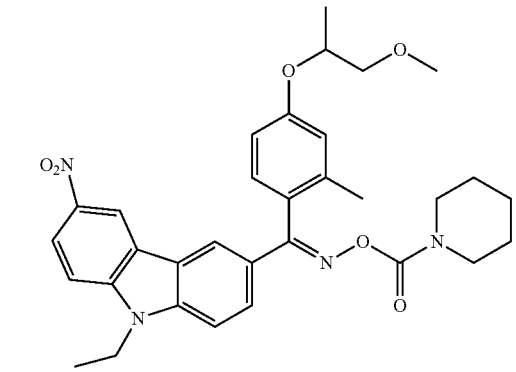

No. 37
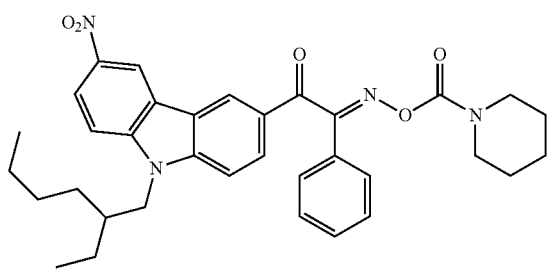

No. 38
No. 39
No. 40
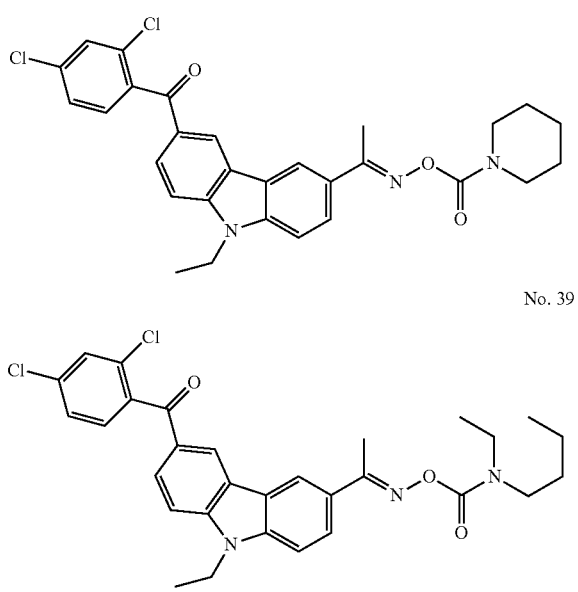

No. 41
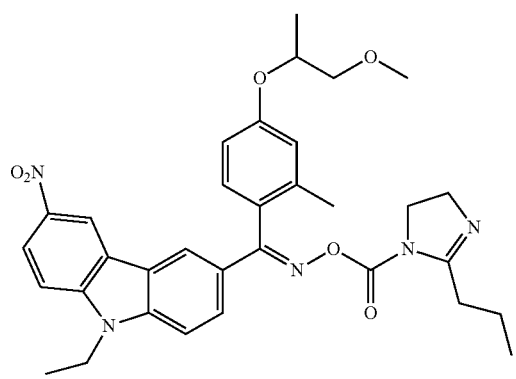

No. 42
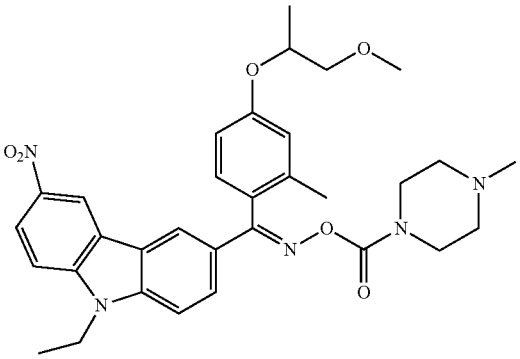

No. 43
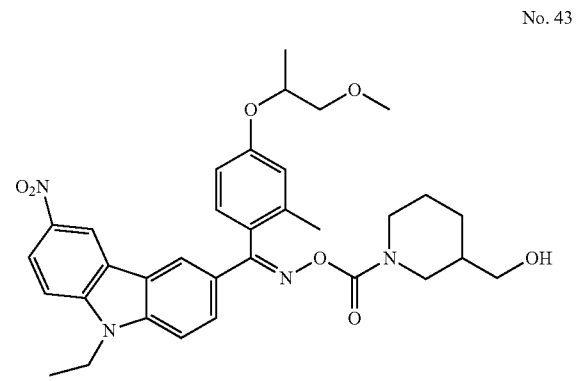 [SMILES: CCn1c2ccc(/C(=N/OC(=O)N3CCCC(CO)C3)c3ccc(OC(C)COC)cc3C)cc2c2cc([N+](=O)[O-])ccc21]

The novel compound (1) may be prepared, for example, according to reaction scheme shown below, which is not deemed to limit the process for the preparation of the compound (1).

Specifically, an oxime compound (2) and an isocyanate compound (3) are allowed to react with each other in the presence of a catalyst in dimethylformamide (DMF) to give a novel compound (1') that corresponds to the compound (1) in which $R^3$ is hydrogen. Thereafter, a group other than hydrogen may be introduced as $R^3$ by introducing an alkyl chain or the like in a usual manner. The compound (1) in which $R^2$ and $R^3$ are taken together to form an imidazole ring together with the nitrogen atom may be synthesized by using carbonyl diimidazole in place of the isocyanate compound (3).

[Chemical Formula 7]

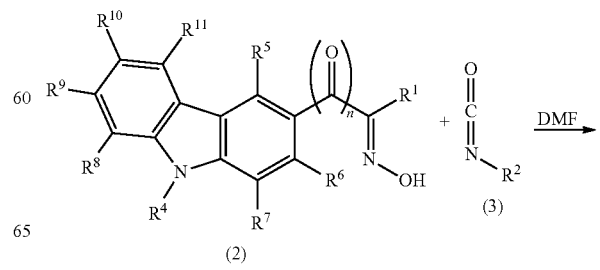

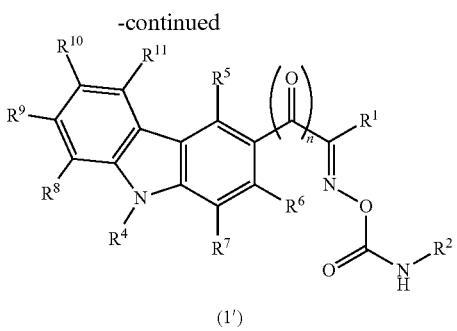

(1')

wherein $R^1$ to $R^{11}$, and n are as defined above.

The novel compound of the invention exhibits high performance of causing a photosensitive resin to cure and high sensitivity to energy rays and is therefore suited for use as a photo-initiator that is a photo-base generator as hereinafter described. It is also useful as a chemically amplified resist and the like.

The photosensitive resin composition of the invention will then be illustrated. The foregoing description about the novel compound of the invention applies to the photosensitive resin composition as appropriate.

(A) Photo-Initiator

The photo-initiator (A) that can be used in the photosensitive resin composition comprises at least one compound (1). The proportion of the compound (1) in the photo-initiator is preferably 1 to 100 mass %, more preferably 50 to 100 mass %.

The content of the photo-initiator (A) in the photosensitive resin composition is preferably 1 to 20 parts by mass, more preferably 1 to 10 parts by mass, per 100 parts by mass of the photosensitive resin composition (B). If the content of the photo-initiator (A) is less than 1 part by mass, the photosensitive resin composition can undercure due to insufficient sensitivity. If it is more than 20 parts by mass, the photosensitive resin composition can generate much volatiles on irradiation with light or heating.

(B) Photosensitive Resin

The photosensitive resin (B) that can be used in the invention is a resin having an anionically polymerizable functional group or a resin of which the curing temperature decreases in the presence of a base as a catalyst. It is a photosensitive resin that polymerizes upon being irradiated with energy rays, such as UV light, or a curing resin that lowers its curing temperature upon being irradiated with energy rays. As used herein, the term "anionically polymerizable functional group" refers to a functional group polymerizable in the presence of a base that is generated by a photo-base generator upon being exposed to active energy rays such as UV light. Examples of the anionically polymerizable functional group include an epoxy group, an episulfide group, a cyclic monomer (e.g., σ-valerolactone or ∈-caprolactam), a catalyst for urethane bond formation between an isocyanate and an alcohol, and a catalyst for Michael addition of a (meth)acryl group. Examples of the photosensitive resin (B) include epoxy resins, polyamide resins, polyurethane resins, nylon resins, and polyester resins. These resins may be used either individually or in combination of two or more thereof. Inter alia, epoxy resins are preferred for rapid reaction progress and good adhesiveness.

The epoxy resins include polyglycidyl ether compounds of mononucleic polyhydric phenol compounds, such as hydroquinone, resorcinol, pyrocatechol, and phloroglucinol; polyglycidyl ether compounds of polynucleic polyhydric phenol compounds, such as dihydroxynaphthalene, biphenol, methylene bisphenol (bisphenol F), methylenebis(o-cresol), ethylidenebisphenol, isopropylidenebisphenol (bisphenol A), 4,4'-dihydroxybenzophenone, isopropylidenebis(o-cresol), tetrabromobisphenol A, 1,3-bis(4-hydroxycumylbenzene), 1,4-bis(4-hydfoxycumylbenzene), 1,1,3-tris(4-hydroxyphenyl)butane, 1,1,2,2-tetra(4-hydroxyphenyl)ethane, thiobisphenol, sulfobisphenol, oxybisphenol, phenol novolak, o-cresol novolak, ethylphenol novolak, butylphenol novolak, octylphenol novolak, resorcin novolak, and terpene phenol; polyglycidyl ethers of polyhydric alcohols, such as ethylene glycol, propylene glycol, butylene glycol, hexanediol, polyglycols, thiodiglycol, glycerol, trimethylolpropane, pentaerythritol, sorbitol, and a bisphenol A-ethylene oxide adduct; homo- or copolymers of glycidyl methacrylate or glycidyl esters of aliphatic, aromatic or alicyclic polybasic acids, such as maleic acid, fumaric acid, itaconic acid, succinic acid, glutaric acid, suberic acid, adipic acid, azelaic acid, sebacic acid, a dimer acid, a trimer acid, phthalic acid, isophthalic acid, terephthalic acid, trimellitic acid, trimesic acid, pyromellitic acid, tetrahydrophthalic acid, hexahydrophthalic acid, and endomethylenetetrahydrophthalic acid; epoxy compounds having a glycidylamino group, such as N,N-diglycidylaniline and bis(4-(N-methyl-N-glycidylamino)phenyl)methane; epoxidized cyclic olefin compounds, such as vinylcyclohexene diepoxide, dicyclopentanediene diepoxide, 3,4-epoxycyclohexylmethyl 3,4-epoxycyclohexanecarboxylate, 3,4-epoxy-6-methylcyclohexylmethyl 6-methylcyclophexanecarboxylate, and bis(3,4-epoxy-6-methylcyclohexylmethyl) adipate; and epoxidized conjugate diene polymers, such as epoxidized polybuadiene, an epoxidized acrylonitrile-butadiene copolymer, and an epoxidized styrene-butadiene copolymer; and heterocyclic compounds, such as triglycidyl isocyanurate. These epoxy resins may be internally crosslinked using an isocyanate-terminated prepolymer or may have their molecular weight increased using a polyhydric active hydrogen compound, e.g., a polyhydric phenol, a polyamine, a carbonyl-containing compound, or a polyphosphoric ester.

Preferred of the above epoxy resins are those having a glycidyl group, particularly those having two or more glycidyl groups per molecule.

The polyamide resins include those prepared from, as an acid dianhydride component, ethylenetetracarboxylic dianhydride, 1,2,3,4-benzenetetracarboxylic dianhydride, 1,2,3,4-cyclohexanetetracarboxylic dianhydride, 2,2',3,3'-benzophenonetetracarboxylic dianhydride, 2,2,3,3-biphenyltetracarboxylic anhydride, or 1,4,5,8-naphthalenetetracarboxylic dianhydride, and, as a diamine component, (o-, m-, or p-)phenylenediamine, (3,3'- or 4,4'-)diaminodiphenyl ether, diaminobenzophenone, or (3,3'- or 4,4'-)diaminodiphenylmethane.

The polyurethane resins include those prepared from, as a diisocyanate component, a polyfunctional isocyanate, such as tolylene diisocyanate, hexamethylene diisocyanate, diphenylmethane diisocyanate, or isophorone diisocyanate, and a polyol (polyfunctional alcohol), such as polyether polyol, polyester polyol, or polycarbonate polyol.

The nylon resins include those prepared from cyclic monomers, such as ∈-caprolactam and lauryl lactam.

The polyester resins include those prepared from cyclic monomers, such as δ-valerolactone and β-propiolactone.

(C) Additive

The photosensitive resin composition of the invention may optionally contain additives, such as inorganic compounds, colorants, latent epoxy curing agents, chain transfer agents, sensitizers, and solvents.

Examples of the inorganic compounds include metal oxides, such as nickel oxide, iron oxide, iridium oxide, titanium oxide, zinc oxide, magnesium oxide, calcium oxide, potassium oxide, silica, and alumina; layered clay minerals, Milori blue, calcium carbonate, magnesium carbonate, cobalt compounds, manganese compounds, glass powder (particularly glass frit), mica, talc, kaolin, ferrocyanides, various metal sulfates, sulfides, selenides, aluminum silicate, calcium silicate, aluminum hydroxide, platinum, gold, silver, and copper. The inorganic compounds are used as, for example, a filler, an antireflection agent, an electrically conductive agent, a stabilizer, a flame retardant, a mechanical strength enhancer, a specific wavelength absorbing agent, an ink repellent agent, and the like.

The colorants includes pigments, dyes, and naturally occurring dyes. The colorants may be used either individually or as a mixture of two or more thereof.

The pigments may be either organic or inorganic, including nitroso compounds; nitro compounds; azo compounds; diazo compounds; xanthene compounds; quinoline compounds; anthraquinone compounds; coumarin compounds; phthalocyanine compounds; isoindolinone compounds; isoindoline compounds; quinacridone compounds; anthanthrone compounds; perynone compounds; perylene compounds; diketopyrrolopyrrole compounds; thioindigo compounds; dioxazine compounds; triphenylmethane compounds; quinophthalone compounds; naphthalenetetracarboxylic acids; metal complex compounds, such as azo dyes and cyanine dyes; lake pigments; carbon black species, such as furnace black, channel black, thermal black, acetylene black, Ketjen black, and lamp black; the carbon blacks recited having been modified or coated with an epoxy resin, the carbon blacks recited having been dispersed in a solvent together with a resin to have 20 to 200 mg/g of the resin adsorbed thereon, the carbon blacks recited having been surface treated with an acid or an alkali, carbon black having an average particle size of 8 nm or greater and a DBP absorption of 90 ml/100 g or less, carbon black having a total oxygen content of 9 mg or more per 100 $m^2$ of its surface area as calculated from the CO and $CO_2$ content in the volatile content at 950° C.; graphite, graphitized carbon black, activated carbon, carbon fiber, carbon nanotube, carbon microcoil, carbon nanohorn, carbon aerogel, fullerene; aniline black, pigment black 7, titanium black; chromium oxide green, Milori blue, cobalt green, cobalt blue, manganese compounds, ferrocyanides, phosphate ultramarine blue, Prussian blue, ultramarine, cerulean blue, viridian, emerald green, lead sulfate, lead yellow, zinc yellow, Bengal red (red iron (III) oxide), cadmium red, synthetic iron black, and amber. The pigments may be used either individually or as a mixture thereof.

Commercially available pigments may be used, including pigment red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; pigment orange 13, 31, 34, 36, 38, 43, 46, 48, 49, 51, 52, 55, 59, 60, 61, 62, 64, 65, and 71; pigment yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; pigment green 7, 10, and 36; pigment blue 15, 15:1, 15:2, 15:3, 15:4, 15:5, 15:6, 22, 24, 56, 60, 61, 62, and 64; and pigment violet 1, 19, 23, 27, 29, 30, 32, 37, 40, and 50.

Examples of the dyes include azo dyes, anthraquinone dyes, indigoid dyes, triarylmethane dyes, xanthene dyes, alizarine dyes, acridine dyes, stilbene dyes, thiazole dyes, naphthol dyes, quinoline dyes, nitro dyes, indamine dyes, oxazine dyes, phthalocyanine dyes, and cyanine dyes. The may be used as a mixture thereof.

Examples of the latent epoxy curing agents include dicyandiamides, modified polyamines, hydrazides, 4,4'-diaminodiphenylsulfone, trifluoroboron-amine complex salts, imidazoles, guanamines, imidazoles, ureas, and melamine.

As the chain transfer agent or the sensitizer, sulfur-containing compounds are generally used, including mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl(4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzoimidazole, 2-mercapto-3-pyridinol, 2-mercaptobenzothiazole, mercaptoacetic acid, trimethylolpropane tris(3-mercaptopropionate), and pentaerythritol tetrakis (3-mercaptopropionate); disulfide compounds obtained by oxidizing the recited mercapto compounds; and iodized alkyl compounds, such as iodoacetic acid, iodopropionic acid, 2-iodoethanol, 2-iodoethanesulfonic acid, and 3-iodopropanesulfonic acid; and aliphatic multifunctional thiol compounds, such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethylolpropane tristhiopropionate, trimethylolpropane tristhioglycolate, pentaerythritol tetrakisthiopropionate, pentaerythritol tetrakisthioglycolate, trishydroxyethyl tristhiopropionate, diethylthioxanthone, diisopropylthioxanthone, compound C1 shown below, trimercaptopropionic acid tris(2-hydroxyethyl)isocyanurate; and KARENZ MT BD1, PE1 and NR1 manufactured by Showa Denko.

[Chemical Formula 8]

Compound No.C1

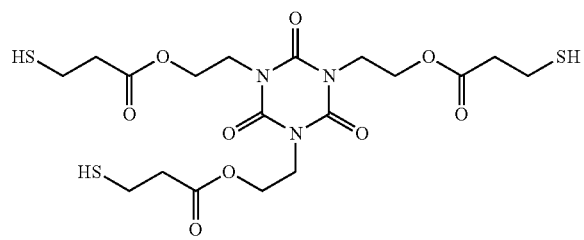

The solvents that can be used in the invention are usually those capable of dissolving or dispersing the above described components (including the photo-initiator (A) and the photosensitive resin (B)). Such solvents include ketones, e.g., methyl ethyl ketone, methyl amyl ketone, diethyl ketone, acetone, methyl isopropyl ketone, methyl isobutyl ketone, cyclohexanone, and 2-heptanone; ethers, such as ethyl ether, dioxane, tetrahydrofuran, 1,2-dimethoxyethane, 1,2-diethoxyethane, and dipropylene glycol dimethyl ether; esters, such as methyl acetate, ethyl acetate, n-propyl acetate, isopropyl acetate, n-butyl acetate, cyclohexyl acetate, ethyl lactate, dimethyl succinate, and Texanol; cellosolves, such as ethylene glycol monomethyl ether and ethylene glycol monoethyl ether; alcohols, such as methanol, ethanol, isopropyl alcohol, n-propanol, isobutanol, n-butanol, and amyl alcohol; ether esters, such as ethylene glycol monomethyl acetate, ethylene glycol monoethyl acetate, propylene glycol 1-monomethyl ether 2-acetate, dipropylene glycol monomethyl ether acetate, 3-methoxybutyl acetate, and ethoxyethyl propionate; BTX solvents (benzene, toluene, xylene, etc.); aliphatic hydrocarbons, such as hexane, heptane, octane, and cyclohexane; terpene hydrocarbon oils, such as turpentine oil, D-limonene, and pinene; paraffinic solvents, such as mineral spirit, Swazol #310 (from Cosmo Matsuyama Oil Co., ltd.), and Solvesso #100 (from Exxon Chemical); halogenated aliphatic hydrocarbons, such as carbon tetrachloride, chloroform, trichloroethylene, methylene chloride, and 1,2-dichloroethane; halogenated aromatic hydrocarbons, such as chlorobenzene; carbitol solvents, aniline, triethylamine, pyridine, acetic acid, acetonitrile, carbon disulfide, N,N-dimethylformamide, N,N-dimethylacetamide, N-methylpyrrolidone, dimethyl sulfoxide, and water. These solvents may be used either individually or as a mixture of two or more thereof.

Preferred of them are ketones and ether esters, particularly propylene glycol 1-monomethyl ether 2-acetate and cyclohexanone in terms of alkali developability, patterning properties, film forming properties, and solubilizing capability.

The amount of the solvent in the photosensitive resin composition of the invention is not particularly limited. The solvent is used in an amount just enough to dissolve or disperse each component to provide a homogeneous liquid or pasty photosensitive resin composition suited for the intended use. Usually, the solvent is preferably used in an amount to result in a solid content (all the components except the solvent) of 10 to 90 mass % in the photosensitive resin composition of the invention.

The photosensitive resin composition of the invention may further contain an organic polymer to provide a cured product with improved characteristics. Examples of such an organic polymer include polystyrene, polymethyl methacrylate, methyl methacrylate-ethyl acrylate copolymers, poly (meth)acrylic acid, styrene-(meth)acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonate, polyvinyl butyral, cellulose esters, polyacrylamide, saturated polyesters, phenol resins, and phenoxy resins.

The amount of the organic polymer, if used, is preferably 10 to 500 parts by mass per 100 parts by mass of the photosensitive resin (B).

The photosensitive resin composition of the invention may furthermore contain a surfactant, a silane coupling agent, a melamine compound, and so forth.

Examples of the surfactant include fluorine-containing surfactants, such as perfluoroalkylphosphoric esters, perfluoroalkylcarboxylic acid salts; anionic surfactants, such as higher fatty acid alkali salts, alkylsulfonic acid salts, and alkylsulfuric acid salts; cationic surfactants, such as higher amine halogenic acid salts and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants; and silicone surfactants. These surfactants may be used in combination thereof.

Examples of the silane coupling agent include those manufactured by Shin-Etsu Chemical Co., Ltd. Preferred of them are those having an isocyanate group, a methacryloyl group, or an epoxy group, such as KBE-9007, KBM-502 and KBE-403.

Examples of the melamine compounds include nitrogen compounds, such as (poly)methylolmelamine, (poly)methylol glycoluril, (poly)methylol benzoguanamine, and (poly)methylolurea, of which all or a part (at least two) of the active methylol groups ($CH_2OH$) are etherified with an alkyl group. Examples of the alkyl groups that constitute the alkyl ether may include methyl, ethyl, and butyl, and the alkyl groups may be the same or different. The methylol groups that are not alkyl-etherified may be self-condensed intramolecularly or may be condensed intermolecularly to form an oligomeric component. Specific examples of the melamine compounds are hexamethoxymethylmelamine, hexabutoxymethylmelamine, tetramethoxymethyl glycoluril, and tetrabutoxymethyl glycoluril, with the alkyl-etherified melamines, such as hexamethoxymethylmelamine and hexabutoxymethylmelamine, being preferred in terms of solubility in a solvent and less likelihood of crystallization from the photosensitive resin composition.

The amounts of the optional components other than the photo-initiator (A) and the photosensitive resin (B), except the inorganic compound, the colorant, and the solvent, in the photosensitive resin composition of the invention are decided as appropriate to the use of the composition with no particular limitation. Preferably, the total amount of the optional components is not more than 50 parts by mass per 100 parts by mass of the photosensitive resin (B).

The photosensitive resin composition of the invention cures upon irradiation with energy rays. The cured product may have an appropriate form according to the intended use. In the formation of a cured product, e.g., of film form, the photosensitive resin composition is applied to a substrate, such as soda glass, quartz glass, semiconductor substrates, metal, paper, or plastics, by a known coating method, such as spin coating, roll coating, bar coating, die coating, curtain coating, printing, or dipping. The photosensitive resin composition may be once applied to a carrier substrate, such as a film, and then transferred to another substrate. There is no restriction on the manner of application.

The sources of energy rays used to cure the photosensitive resin composition of the invention include ultrahigh pressure mercury lamps, high pressure mercury lamps, medium pressure mercury lamps, low pressure mercury lamps, mercury vapor arc lamps, xenon arc lamps, carbon arc lamps, metal halide lamps, fluorescent lamps, tungsten lamps, excimer lamps, germicidal lamps, light-emitting diodes, and CRT light sources. Electromagnetic energy rays of wavelengths of 2000 to 7000 Å emitted from these light sources and high-energy rays, such as electron beams, X rays, and radial rays are useful. Preferred light sources are ultrahigh pressure mercury lamps, mercury vapor arc lamps, carbon arc lamps, and xenon arc lamps that emit light of 300 to 450 nm A laser direct imaging technology is beneficial in the interests of productivity, resolution, and pattern position accuracy, in which a laser beam as an exposure light source is directed to the photosensitive resin composition without using a mask to directly write an image based on digital information, e.g., from a computer. A laser beam having a wavelength of 340 to 430 nm is suitably used. Lasers emitting light of from the visible to infrared region may also be used, such as excimer lasers, nitrogen lasers, argon ion lasers, helium cadmium lasers, helium neon lasers, krypton ion lasers, various semiconductor lasers, and YAG lasers. When these lasers are used, a sensitizing dye that absorbs the light of the region from visible to infrared is preferably added.

In order for the photosensitive resin composition of the invention to cure, it is usually necessary that the irradiation with energy rays be followed by heating. Heating to a temperature of around 40° to 150° C. is recommended in terms of curing rate.

The photosensitive resin composition of the invention has unlimited application. It finds use in, for example, photocuring paints or varnishes; photocuring adhesives; printed boards; color filters for liquid crystal color displays, such as TV monitors, PC monitors, personal digital assistances, and digital cameras; color filters for CCD image sensors; electrode materials for plasma display panels; powder coatings; printing inks; printing plates; adhesives; compositions for dental use; gel coats; photoresists for electronics; electroplating resists; etching resists; dry films; soldering resists; resists used in the manufacture of color filters of various displays or in the formation of structures of plasma display panels, electroluminescent displays, and LCDs; encapsulating compositions for electric/electronic components; solder resists; magnetic recording materials; fine machine parts; waveguides; optical switches; plating masks; etching masks; color test systems; glass fiber cable coatings; screen printing stencils; materials for making a three-dimensional object by stereolithography; holographic recording materials; image recording materials; fine electronic circuits; decolorizing materials; decolorizing materials for image recording materials; decolorizing materials for image recording materials using microcapsules; photoresist materials for printed wiring boards; photoresist materials for direct write using UV and visible lasers; and photoresist materials or protective layers used to form dielectric layers in the fabrication of multilayered printed circuit boards.

The photosensitive resin composition of the invention is also useful in the formation of spacers for LCD panels and the formation of protrusions for vertical-alignment LCD elements. The photosensitive resin composition is particularly useful for simultaneously forming spacers and protrusions for vertical-alignment LCD elements.

The spacers for LCD panels are preferably produced through the steps of (1) forming a coating film of the photosensitive resin composition of the invention on a substrate, (2) irradiating the film with energy rays (light) through a mask having a predetermined pattern, (3) baking the exposed film, (4) developing the exposed film, and (5) heating the developed film.

The photosensitive resin composition of the invention containing the colorant is suited for use as a resist forming pixels of each color (e.g., RGB) or a black matrix resist forming barrier ribs between pixels in the fabrication of color filters. When the photosensitive resin composition of the invention contains an ink repellent agent, it is suitable as a black matrix resist to form barrier ribs with a profile angle of 50° or greater in inkjet-printed color filters. For that use, a fluorine-containing surfactant or a composition containing a fluorine-containing surfactant is suitably added as the ink repellent agent.

In the case when the photosensitive resin composition of the invention is used to form barrier ribs in the inkjet-printed color filters, an optical element is produced by forming barrier ribs of the photosensitive resin composition of the invention, transferring the barrier ribs to a substrate to partition the substrate into recessed portions, and filling the recessed portions with droplets by inkjet method to form image areas. The droplets preferably contain a colorant so that the image areas may be colored. In that case, the optical element produced by the process described has, on the substrate, at least an array of pixels formed of a plurality of colored portions and barrier ribs separating the colored portions from one another.

The photosensitive resin composition of the invention can also be used as a composition for forming a protective film or an insulating film. For that use, the composition may contain an ultraviolet absorber, an alkylated and/or acrylated melamine, and a mono- or bifunctional (meth)acrylate monomer containing an alcoholic hydroxyl group in its molecule and/or silica sol.

The insulating film is used as an insulating resin layer formed on a release support to provide a laminate. The laminate is preferably developable with an aqueous alkali solution, and the insulating resin layer preferably has a thickness of 10 to 100 nm.

The photosensitive resin composition of the invention may be formulated as a photosensitive paste composition by addition of the inorganic compound. The photosensitive paste composition may be used to form baked patterns of plasma display panels, such as barrier rib patterns, dielectric patterns, electrode patterns, and black matrix patterns.

EXAMPLES

The invention will now be illustrated in greater detail with reference to Examples and Comparative Examples, but it should be understood that the invention is not deemed to be limited thereto.

Examples 1 through 12 describe the synthesis of the novel compounds of the invention (photo-initiators). Examples 13 to 16 and Comparative Example 1 describe evaluation of the photo decomposability of the novel compounds of the invention and a comparative compound. Examples 17 to 20 and Comparative Examples 2 and 3 describe evaluation of amine generating performance of the novel compounds of the invention and comparative compounds. Example 21 and Comparative Example 4 describe the preparation and evaluation of photosensitive resin compositions.

Example 1

Synthesis of compound No. 1

To a mixture of 50.0 g (108 mmol) of (E)-(9-ethyl-6-nitro-9H-carbazol-3-yl) (4-(1-methoxypropan-2-yl)oxy)-2-methylphenyl)methanone oxime and 242 g of dehydrated DMF was added 21.1 g (130 mmol) of carbonyl diimidazole (CDI), followed by stirring at 24° C. for 3 hours. Water and ethyl acetate were added to the reaction mixture to conduct oil-water separation. The organic layer was washed with water, dried over anhydrous magnesium sulfate, and filtered, followed by solvent removal. The resulting crude product weighing 42.7 g was crystallized from 220 g of chloroform and 128 g of dibutyl ether to give 6.6 g (yield: 11.0%) of a yellow solid, which was identified to be compound No. 1 as a result of UV spectrum ($\lambda_{max}$, ∈), TG-DTA (melting temperature/° C., extrapolated decomposition temperature/° C.), IR spectrum, and $^1$H-NMR analyses. The analytical results are shown in Tables 1 to 3.

Example 2

Synthesis of Compound No. 2

To a solution of 6.00 g (13 mmol) of (E)-(9-ethyl-6-nitro-9H-carbazol-3-yl) (4-((1-methoxypropan-2-yl)oxy)-2-methylphenyl)methanone oxime and 0.2 g of Adekastab BT11 (dibutyltin laurate, from ADEKA) in 38 g of dehydrated DMF was added 5.1 g (43 mmol) of phenyl isocyanate, followed by stirring at 25° C. for 6 hours. Water and ethyl acetate were added to the reaction mixture to conduct oil-water separation. The organic layer was washed with water, dried over anhydrous magnesium sulfate, and filtered, followed by solvent removal. The resulting crude product weighing 9.6 g was purified by silica gel column chromatography to give 2.3 g (yield: 34.8%) of a pale yellow solid, which was identified to be compound No. 2 as a result of UV spectrum ($\alpha_{max}$, ∈), TG-DTA (melting temperature/° C., extrapolated decomposition temperature/° C.), IR spectrum, and $^1$H-NMR analyses. The analytical results are shown in Tables 1 to 3.

Example 3

Synthesis of Compound No. 3

To a solution of 30.0 g (65 mmol) of (E)-(9-ethyl-6-nitro-9H-carbazol-3-yl) (4-((1-methoxypropan-2-yl)oxy)-2-methylphenyl)methanone oxime and 2.9 g of Adekastab BT11 (dibutyltin laurate, from ADEKA) in 182 g of dehydrated DMF was added 15.4 g (156 mmol) of butyl isocyanate, followed by stirring at 25° C. for 8 hours. Water and ethyl acetate were added to the reaction mixture to conduct oil-water separation. The organic layer was washed with water, dried over anhydrous magnesium sulfate, and filtered, followed by solvent removal. The resulting crude product weighing 58.5 g was purified by silica gel column chromatography to give 20.5 g (yield: 56.3%) of a yellow solid, which was identified to be compound No. 3 as a result of UV spectrum ($\lambda_{max}$, ∈), TG-DTA (melting temperature/° C., extrapolated decomposition temperature/° C.), IR spectrum, and $^1$H-NMR analyses. The analytical results are shown in Tables 1 to 3.

Example 4

Synthesis of Compound No. 16

A solution of 4.00 g (8.48 mmol) of (Z)-1-(9-(2-ethylhexyl)-6-nitro-9H-carbazol-3-yl)-2-(hydroxyimino)-2-phenylethanone in 14.40 g of dehydrated DMF was cooled to 5° C., and 1.65 g (10.18 mmol) of di(1H-imidazol-1-yl)methanone was added thereto, followed by stirring at 5° C. for 2 hours. Water and ethyl acetate were added to the reaction mixture to conduct oil-water separation. The organic layer was washed with water, dried over anhydrous magnesium sulfate, and filtered, followed by solvent removal. The resulting crude product weighing 3.50 g was purified by silica gel column chromatography to give 2.5 g (yield: 52.1%) of a pale yellow solid, which was identified to be compound No. 16 as a result of UV spectrum ($\lambda_{max}$, ∈), TG-DTA (melting temperature/° C., extrapolated decomposition temperature/° C.), IR spectrum, and $^1$H-NMR analyses. The analytical results are shown in Tables 1 to 3.

Example 5

Synthesis of Compound No. 36

A mixture of 9.23 g of (9-ethyl-6-nitro-9H-carbazol-3-yl) (4-((1-methoxypropan-2-yl)oxy)-2-methylphenyl)methanone oxime, 4.05 g of triethylamine, and 75 g of dichloromethane was cooled to 5° C. While stirring, a solution of 4.43 g of p-nitrophenyl chlorocarbonate in 15 g of dichloromethane was added dropwise thereto over 30 minutes. The temperature of the mixture was elevated up to room temperature, at which the mixture was stirred for 1 hour. The reaction mixture was again cooled to 5° C., and 1.87 g of piperidine was added thereto dropwise. The temperature was raised to room temperature, at which the mixture was stirred for 1 hour. The solvent was removed by evaporation under reduced pressure, the residue was extracted with ethyl acetate, and the extract was washed with two portions of a 5% aqueous solution of sodium hydroxide and then four portions of water, and dried over anhydrous magnesium sulfate. The solvent was removed by evaporation under reduced pressure, and the residue was purified by crystallization and dried under reduced pressure to give 6.84 g (ODS purity: 99%; yield: 60%) of yellow crystals, which were identified to be compound No. 36 as a result of UV spectrum ($\lambda_{max}$, ∈), TG-DTA (melting temperature/° C., extrapolated decomposition temperature/° C.), IR spectrum, and $^1$H-NMR analyses. The analytical results are shown in Tables 1 to 3.

Example 6

Synthesis of Compound No. 37

The procedure of Example 5 was repeated at the same equivalent ratio as in Example 5, except for replacing the (9-ethyl-6-nitro-9H-carbazol-3-yl) (4-((1-methoxypropan-2-yl)oxy)-2-methylphenyl)methanone oxime as used in Example with 1.18 g of 1-(9-(2-ethylhexyl)-6-nitro-9H-carbazol-3-yl)-2-(hydroxyimino)-2-phenylethanone. The crude product as obtained was purified by silica gel column chromatography using hexane/ethyl acetate (=4/1→3/1) to afford 0.65 g (ODS purity: 99%; yield: 45%) as a pale yellow foam.

Example 7

Synthesis of Compound No. 38

The procedure of Example 5 was repeated at the same equivalent ratio as in Example 5, except for replacing the (9-ethyl-6-nitro-9H-carbazol-3-yl) (4-((1-methoxypropan-2-yl)oxy)-2-methylphenyl)methanone oxime as used in Example with 1.23 g of (2,4-dichlorophenyl) (9-ethyl-6-(1-(hydroxyimino)ethyl)-9H-carbazol-3-yl)methanone. The crude product as obtained was purified by crystallization from cyclopentyl methyl ether and washed with hot ethyl acetate to afford 0.51 g (ODS purity: 94%; yield: 34%) as pale yellow crystals.

Example 8

Synthesis of Compound No. 39

The procedure of Example 5 was repeated at the same equivalent ratio as in Example 5, except for replacing the (9-ethyl-6-nitro-9H-carbazol-3-yl) (4-((1-methoxypropan- 2-yl)oxy)-2-methylphenyl)methanone oxime as used in Example with 1.23 g of (2,4-dichlorophenyl) (9-ethyl-6-(1-(1-hydroxyimino)ethyl)-9H-carbazol-3-yl)methanone and replacing piperidine with ethylbutylamine. The crude product as obtained was purified by silica gel column chromatography using hexane/ethyl acetate (3/2) to give 1.06 g (ODS purity: 99%; yield: 64%) as a pale brown foam.

Example 9

Synthesis of Compound No. 40

The procedure of Example 5 was repeated at the same equivalent ratio as in Example 5, except for replacing the (9-ethyl-6-nitro-9H-carbazol-3-yl) (4-((1-methoxypropan-2-yl)oxy)-2-methylphenyl)methanone oxime as used in Example with 1.23 g of (9-ethyl-6-(1-hydroxyimino)ethyl)-9H-carbazol-3-yl) (o-tolyl)methanone. The crude product as obtained was purified by silica gel column chromatography using hexane/ethyl acetate (3/2) to give 0.79 g (ODS purity: 99%; yield: 49%) as a pale brown foam.

Example 10

Synthesis of Compound No. 41

The procedure of Example 5 was repeated at the same equivalent ratio as in Example 5, except for replacing the piperidine as used in Example 5 with 2-propyl-2-imidzoline. The crude product as obtained was purified by silica gel column chromatography using hexane/ethyl acetate (5/1) to give 1.13 g (ODS purity: 86%; yield: 63%) as yellow crystals.

Example 11

Synthesis of Compound No. 42

The procedure of Example 5 was repeated at the same equivalent ratio as in Example 5, except for replacing the piperidine as used in Example 5 with N-methylpiperazine. The crude product as obtained was purified by silica gel column chromatography using hexane/ethyl acetate (5/1) to give 4.66 g (ODS purity: 98%; yield: 79%) as yellow crystals.

Example 12

Synthesis of Compound No. 43

The procedure of Example 5 was repeated at the same equivalent ratio as in Example 5, except for replacing the piperidine as used in Example 5 with 3-piperidinemethanol. The crude product as obtained was purified by silica gel column chromatography using ethyl acetate/methanol (10/1) to give 4.55 g (ODS purity: 99%; yield: 75%) as orange yellow crystals.

TABLE 1

| Example | Compound | $\lambda_{max}$*[1] (nm) | $\epsilon$ | Melting Temp. (° C.) | Extrapolated Decomposition Temp. (° C.) |
|---|---|---|---|---|---|
| 1 | No. 1 | 369 | 7.7E+03 | — | 147 |
| 2 | No. 2 | 370 | 6.4E+03 | — | 81 |
| 3 | No. 3 | 370 | 6.5E+03 | — | 173 |
| 4 | No. 16 | 366 | 2.4E+04 | 167 | 183 |
| 5 | No. 36 | 368 | 1.3E+04 | 153 | 270 |
| 6 | No. 37 | 363 | 2.0E+04 | — | 243 |
| 7 | No. 38 | 344 | 1.9E+04 | 206 | 242 |
| 8 | No. 39 | 344 | 2.0E+04 | — | 260 |
| 9 | No. 40 | 340 | 1.9E+04 | — | 262 |
| 10 | No. 41 | 372 | 1.3E+04 | — | 200 |
| 11 | No. 42 | 372 | 1.3E+04 | — | 257 |
| 12 | No. 43 | 374 | 1.3E+04 | — | 241 |

*[1]In chloroform in Examples 1 to 4 and methanol in Examples 5 to 12.

TABLE 2

| Example | Compound | IR absorption spectrum (cm$^{-1}$) |
|---|---|---|
| 1 | No. 1 | 3119, 2974, 2927, 1793, 1611, 1572, 1514, 1486, 1449, 1381, 1323, 1293, 1275, 1235, 1176, 1144, 1112, 1096, 1013, 977, 912, 888, 865, 827, 812, 793, 751, 730, 650 |
| 2 | No. 2 | 3356, 3268, 3064, 2980, 2931, 1745, 1712, 1602, 1545, 1516, 1485, 1444, 1361, 1329, 1275, 1236, 1200, 1155, 1130, 1097, 1019, 977, 753 |
| 3 | No. 3 | 3399, 2958, 2932, 2873, 1736, 1630, 1602, 1513, 1499, 1485, 1379, 1329, 1275, 1236, 1174, 1154, 1129, 1097, 973, 936, 752 |
| 4 | No. 16 | 2959, 2931, 2873, 1800, 1665, 1625, 1592, 1583, 1513, 1485, 1466, 1456, 1379, 1327, 1313, 1276, 1233, 1201, 1142, 1093, 998, 956, 930, 917, 891, 873, 851, 828, 801, 760, 745, 683, 651, 630, 544 |
| 5 | No. 36 | 2933, 1730, 1602, 1512, 1499, 1450, 1425, 1322, 1225, 1139, 1128, 1096, 1051, 1019, 998, 973, 922, 885, 872, 848, 812, 748, 728, 655, 634. |
| 6 | No. 37 | 2927, 2855, 1728, 1666, 1626, 1593, 1514, 1481, 1420, 1330, 1306, 1219, 1197, 1129, 1091, 1014, 950, 911, 797, 744, 689, 651, 627. |
| 7 | No. 38 | 2980, 2933, 2863, 1718, 1663, 1623, 1587, 1426, 1372, 1351, 1320, 1307, 1285, 1276, 1256, 1227, 1141, 1162, 1130, 1098, 1047, 1021, 999, 962, 932, 903, 868, 819, 779, 759, 747, 714, 636, 530, 495, 428. |
| 8 | No. 39 | 2929, 2871, 1720, 1657, 1626, 1587, 1484, 1468, 1413, 1371, 1289, 1272, 1239, 1141, 1126, 1100, 1038, 986, 957, 934, 916, 813, 796, 756, 716, 631, 575, 497. |
| 9 | No. 40 | 2932, 2853, 1716, 1650, 1626, 1590, 1417, 1295, 1269, 1249, 1222, 1127, 1107, 1046, 1018, 987, 918, 807, 749, 733, 632. |
| 10 | No. 41 | 2964, 2930, 2874, 1732, 1642, 1599, 1522, 1482, 1452, 1358, 1305, 1232, 1093, 985, 959, 890, 864, 813, 794, 749, 728 |

TABLE 2-continued

| Example | Compound | IR absorption spectrum (cm$^{-1}$) |
|---|---|---|
| 11 | No. 42 | 2937, 2792, 1730, 1604, 1512, 1487, 1449, 1415, 1310, 1275, 1224, 1114, 1064, 1003, 987, 977, 943, 867, 814, 791, 741, 728 |
| 12 | No. 43 | 3431, 2975, 2920, 2856, 1709, 1599, 1512, 1498, 1482, 1466, 1422, 1324, 1230, 1173, 1110, 1046, 989, 889, 812, 750, 728 |

TABLE 3

| Example | Compound | solvent | $^1$H-NMR (ppm (multiplicity, proton number)) |
|---|---|---|---|
| 1 | No. 1 | DMSO | 1.29 (d, 3H), 1.37 (t, 3H), 2.14 (s, 3H), 3.32 (s 3H), 3.52 (m, 2H), 4.58 (m, 2H), 4.76 (m, 1H), 7.00 (d, 1H), 7.07 (s, 2H), 7.21 (s, 1H), 7.22 (d, 1H), 7.83 (s, 1H), 7.87 (m, 3H), 8.38 (d, 1H), 8.61 (s, 1H), 9.33 (s, 1H) |
| 2 | No. 2 | CDCl$_3$ | 1.41 (d, 3H), 1.50 (t, 3H), 2.18 (s, 3H), 3.46 (s, 3H), 3.53 (q, 1H), 3.66 (q, 1H), 4.44 (m, 2H), 4.64 (m, 1H), 6.87 (d, 1H), 6.92 (s, 1H), 7.07 (d, 1H), 7.14 (m, 2H), 7.24-7.36 (m, 3H), 7.46 (d, 2H), 7.52 (brs, 1H), 7.96 (d, 1H), 8.16 (s, 1H), 8.40 (d, 1H), 8.96 (s, 1H) |
| 3 | No. 3 | CDCl$_3$ | 0.96 (t, 3H), 1.38-1.44 (m, 5H), 1.48 (t, 3H), 1.57-1.63 (m, 2H), 2.14 (s, 3H), 3.33-3.38 (m, 2H), 3.45 (s, 3H), 3.52 (q, 1H), 3.64 (q, 1H), 4.43 (m, 2H), 4.62 (m, 1H), 6.31 (m, 1H), 6.84 (d, 1H), 6.89 (s, 1H), 7.02 (d, 1H), 7.44 (d, 2H), 7.84 (d, 1H), 8.17 (s, 1H), 8.40 (d, 1H), 8.95 (s, 1H) |
| 4 | No. 16 | CDCl$_3$ | 0.83 (t, 3H), 0.92 (t, 3H), 1.21-1.43 (m, 8H), 2.03 (t, 1H), 4.25 (m, 2H), 6.88 (s, 1H), 7.10 (s, 1H), 7.47 (t, 3H), 7.56 (d, 2H), 7.67 (s, 1H), 7.85 (d, 2H), 8.22 (d, 1H), 8.24 (d, 1H), 8.73 (s, 1H), 9.02 (d, 1H) |
| 5 | No. 36 | CDCl$_3$ | 8.94 (d, 1H), 8.39 (dd, 1H), 8.18 (d, 1H), 8.15 (dd, 1H), 7.47 (d, 1H), 7.43 (d, 1H), 7.08 (d, 1H), 6.95 (s, 1H), 6.90 (dd, 1H). 4.67 (ddt, 1H), 4.44 (q, 2H), 3.68 (dd, 1H), 3.57 (dd, 1H), 3.48 (s, 3H), 3.48 (br, 2H), 3.01 (br, 2H), 2.18 (s, 3H), 1.56 (br, 4H), 1.50 (t, 3H), 1.41 (d, 3H), 1.39 (br, 2H). |
| 6 | No. 37 | CDCl$_3$ | 9.07 (d, 1H), 8.81 (s, 1H), 8.45 (dd, 1H), 8.19 (d, 1H), 7.84 (d, 2H), 7.54-7.41 (m, 5H), 4.27 (d, 2H), 3.37 (br, 2H), 2.91 (br, 2H), 2.10-2.00 (m, 1H), 1.50-0.99 (m, 14H), 0.94 (t, 3H), 0.86 (t, 3H). |
| 7 | No. 38 | CDCl$_3$ | 8.49 (s, 1H), 8.44 (s, 1H), 8.13 (d, 1H), 7.96 (d, 1H), 7.55 (s, 1H), 7.49-7.41 (m, 4H), 4.42 (q, 2H), 3.57 (br, 4H), 2.49 (s, 3H), 1.65 (br, 6H), 1.49 (t, 3H). |
| 8 | No. 39 | CDCl$_3$ | 8.50 (d, 1H), 8.44 (d, 1H), 8.13 (dd, 1H), 7.97 (dd, 1H), 7.56 (d, 1H), 7.49-7.39 (m, 4H), 4.42 (q, 2H), 3.42 (q, 2H), 3.36 (t, 2H), 2.49 (s, 3H), 1.65 (s, 2H), 1.49 (t, 3H), 1.40 (q, 2H), 1.30-1.20 (m, 3H), 0.98 (t, 3H). |
| 9 | No. 40 | CDCl$_3$ | 8.49 (d, 1H), 8.44 (d, 1H), 8.13 (dd, 1H), 7.99 (dd, 1H), 7.48-7.29 (m, 6H), 4.42 (q, 2H), 3.57 (br, 4H), 2.48 (s, 3H), 2.36 (s, 3H), 1.65 (br, 6H), 1.49 (t, 3H). |
| 10 | No. 41 | CDCl$_3$ | 8.94 (d, 1H), 8.38 (dd, 1H), 8.19 (d, 1H), 8.08 (dd, 1H), 7.47 (d, 1H), 7.43 (d, 1H), 7.08 (d, 1H), 6.94 (s, 1H), 6.91 (d, 1H), 4.66 (tq, 1H), 4.44 (q, 1H), 3.73 (t, 2H), 3.68-3.64 (m, 1H), 3.57-3.54 (m, 1H), 3.46 (s, 1H), 3.51-3.40 (m, 1H), 2.61-2.49 (m, 2H), 2.17 (s, 3H), 1.65 (tq, 2H), 1.50 (t, 3H), 1.40 (d, 3H), 0.95 (t, 3H). |
| 11 | No. 42 | CDCl$_3$ | 8.93 (s, 1H), 8.38 (d, 1H), 8.16 (s, 1H), 8.13 (d, 1H), 7.45 (d, 1H), 7.42 (d, 1H), 7.07 (d, 1H), 6.93 (s, 1H), 6.89 (d, 1H), 4.66 (sex, 1H), 4.43 (q, 2H), 3.66 (dd, 1H), 3.55 (dd, 1H), 3.48 (s, 3H), 3.09 (br, 2H), 2.34 (br, 2H), 2.26 (s, 3H), 2.20 (br, 2H), 2.16 (s, 3H), 1.66 (br, 2H), 1.49 (t, 3H), 1.39 (d, 3H) |
| 12 | No. 43 | CDCl$_3$ | 8.93 (s, 1H), 8.38 (d, 1H), 8.18 (br, 2H), 7.47 (d, 1H), 7.43 (d, 1H), 7.07 (d, 1H), 6.94 (s, 1H), 6.90 (d, 1H), 4.65 (sex, 1H), 4.43 (q, 2H), 4.05 (br, 1H), 3.85 (br, 1H), 3.66 (dd, 1H), 3.55 (dd, 1H), 3.46 (s, 3H), 3.42 (br, 1H), 3.19 (br, 1H), 2.84 (br, 1H), 2.45 (br, 1H), 2.18 (s, 3H), 1.90 (br, 1H), 1.77 (br, 1H), 1.68 (br, 1H), 1.49 (t, 3H), 1.48 (br, 1H), 1.39 (d, 3H), 1.28 (br, 1H) |

Examples 13 to 16 and Comparative Example 1

Evaluation of Photo Decomposability

The compound shown in Table 4 below was dissolved in a 90/10 (by volume) mixture of acetonitrile and water to prepare a 100 ppm solution as a test sample. The sample solution was irradiated with light from an ultrahigh pressure mercury lamp at 100 mJ/cm$^2$, 1000 mJ/cm$^2$, and 10000 mJ/cm$^2$ (integrated value based at i-line). The photo-decomposability of the compound shown in Table 4 was examined by an HPLC method under the conditions described below. The peak of the chromatogram of the unexposed sample was taken as zero, and the amount of decomposition was represented by percentage.

HPLC:
Instrument: Available from Hitachi High Technologies, equipped with UV detector L-2400
Mobile phase: acetonitrile/water/triethylamine/acetic acid=90/10/0.2/0.2
Flow rate: 1 ml/min
Column: Inertsil ODS-2
Column temperature: 40° C.
Detection: 254 nm

TABLE 4

| | | Irradiation Dose (mJ/cm$^2$) | | |
|---|---|---|---|---|
| | Compound | 100 | 1000 | 10000 |
| Example 13 | No. 1 | 32 | 90 | >95 |
| Example 14 | No. 2 | 19 | 90 | >95 |

TABLE 4-continued

| | Compound | Irradiation Dose (mJ/cm²) | | |
| --- | --- | --- | --- | --- |
| | | 100 | 1000 | 10000 |
| Example 15 | No. 3 | 22 | 80 | >95 |
| Example 16 | No. 16 | 40 | >95 | >95 |
| Comparative Example 1 | comparative compound 1*² | 0 | 5 | 45 |

*²*

Comparative compound 1

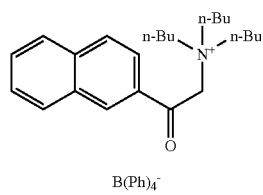

The results in Table 4 prove that the novel compounds of the invention exhibit high UV decomposability so that they generate a good amount of a base on UV decomposition to provide a curing composition with high sensitivity in curing.

Examples 17 to 20 and Comparative Examples 2 and 3

Determination of Amine Generation

In 28 g of a 1/1 (by weight) mixed solvent of methanol/tetrahydrofuran was dissolved 0.04 mmol of the compound shown in Table 5 to prepare a test compound solution. A 3.5 g portion of the solution was irradiated with light from an ultrahigh pressure mercury lamp at 10000 mJ/cm² (integrated value based at i-line). A 2.8 g portion of the irradiated solution was diluted with methanol and analyzed on Automatic Titrator COM-1600 from Hiranuma Sangyo Co., Ltd. using a 0.01 mol/1 hydrochloric acid solution as a titrant. A methanol solution of 0.04 mmol dimethylbenzylamine was titrated as a reference. The amine generation was determined from the titration values. The results obtained are shown in Table 5.

TABLE 5

| | Compound | MeOH/THF = 1/1 (wt/wt) Solution |
| --- | --- | --- |
| Example 17 | No. 36 | 80 |
| Example 18 | No. 31 | 56 |
| Example 19 | No. 39 | 68 |
| Example 20 | No. 40 | 68 |
| Comparative Example 2 | comparative compound 2*³ | 46 |
| Comparative Example 3 | comparative compound 3*⁴ | 48 |

*³

Comparative compound 2

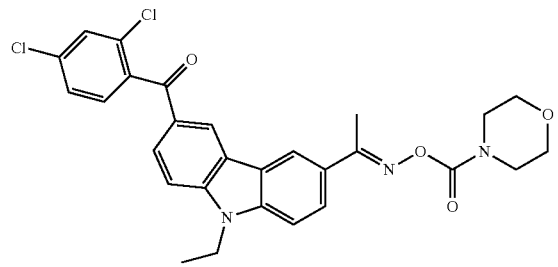

*⁴

Comparative compound 3

Example 21 and Comparative Example 4

Preparation and Evaluation of Photosensitive Resin Compositions

Photosensitive resin compositions of Example 21 and Comparative Example 4 were prepared by mixing and kneading 5 parts by mass of the compound shown in Table 6 below as a photo-initiator (A), 52 parts by mass of a bisphenol F glycidyl ether EP-4901 (from ADEKA Corp.) as a photosensitive rein (B), and 43 parts by mass of an epoxy curing agent Karenz MT BD1 (from Showa Denko K.K.) as an additive in a three-roll mill Each of the resulting photosensitive resin compositions was (a) heated at 60° C. for 60 minutes or (b) irradiated with UV light from an ultrahigh pressure mercury lamp at 200 mJ/cm², followed by heating at 60° C. for 60 minutes, and the curing ratio was determined. The curing ratio was expressed relatively, with the ratio of the peak intensity at 3450 cm⁻¹ to the peak intensity at 1510 cm⁻¹ in the FI-IR spectrum of a cured product obtained by irradiating the photosensitive resin composition with UV light at 5000 mJ/cm², followed by heating at 120° C. for 60 minutes being taken as a curing ratio of 100%. The results obtained are shown in Table 6.

TABLE 6

| | Compound | Curing Ratio (%) | |
| --- | --- | --- | --- |
| | | 0 mJ/cm² | 200 mJ/cm² |
| Example 21 | No. 1 | 0 | >95 |
| Comparative Example 4 | comparative compound 1 | 0 | 34 |

It is seen from Table 6 that, although neither the photosensitive resin composition of the invention or the comparative composition cures unless irradiated with light, the photosensitive resin composition of the invention shows a high curing ratio when irradiated and then heated. It is thus obvious that the novel compound of the invention is an excellent photo-initiator.

The invention claimed is:
1. A compound represented by general formula (1):

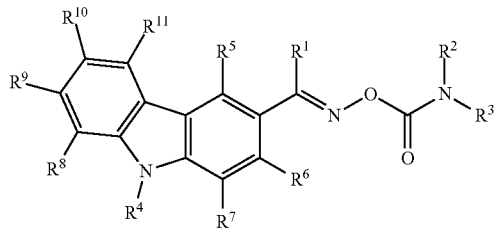

wherein R¹ represents an unsubstituted or substituted aliphatic hydrocarbon group having 1 to 20 carbon atoms or an unsubstituted or substituted aromatic hydrocarbon group having 6 to 20 carbon atoms,
R² and R³ are taken together to form a ring containing a nitrogen atom and a carbon atom,
R⁴ represents an unsubstituted or substituted aliphatic hydrocarbon group having 1 to 20 carbon atoms, an unsubstituted or substituted aromatic hydrocarbon group having 6 to 20 carbon atoms, or an unsubstituted or substituted heterocyclic group having 2 to 20 carbon atoms,
R⁵, R⁶, R⁷, R⁸, R⁹, and R¹¹ each independently represent a hydrogen atom, a cyano group, a halogen atom, or an unsubstituted aliphatic hydrocarbon group having 1 to 20 carbon atoms, and
R¹⁰ is a nitro group.

2. The compound according to claim 1, wherein R¹ in general formula (1) is an unsubstituted or substituted aromatic hydrocarbon group having 6 to 20 carbon atoms.

3. The compound according to claim 1, selected from the group consisting of:

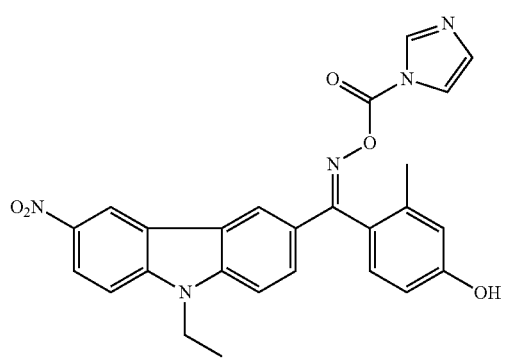

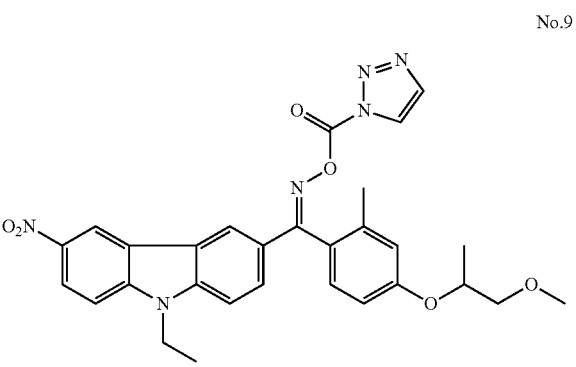

-continued

No. 41

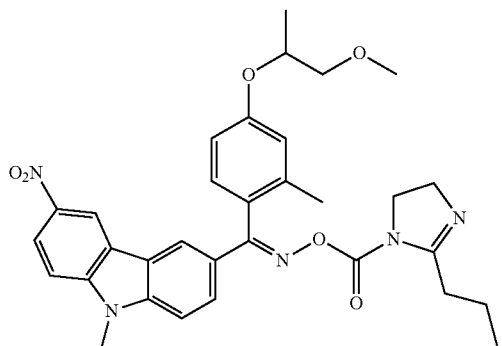

No. 42

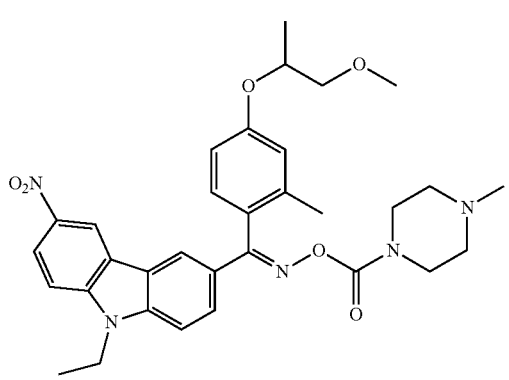

No. 43

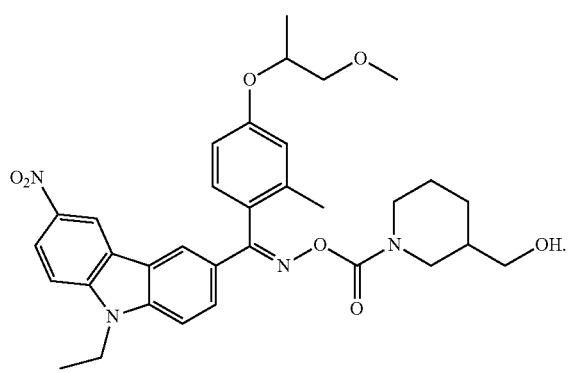

4. The compound according to claim 1, wherein $R^1$ in general formula (1) is a substituted or unsubstituted phenyl group.

5. A photosensitive resin composition comprising (A) a photo-initiator comprising at least one compound represented by general formula (1):

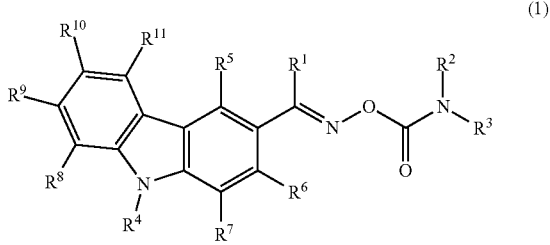

(1)

wherein $R^1$ represents an unsubstituted or substituted aliphatic hydrocarbon group having 1 to 20 carbon atoms, or an unsubstituted or substituted aromatic hydrocarbon group having 6 to 20 carbon atoms, $R^2$ and $R^3$ are taken together to form a ring containing a nitrogen atom and a carbon atom, $R^4$ represents an unsubstituted or substituted aliphatic hydrocarbon group having 1 to 20 carbon atoms, an unsubstituted or substituted aromatic hydrocarbon group having 6 to 20 carbon atoms, or an unsubstituted or substituted heterocyclic group having 2 to 20 carbon atoms, $R^5$, $R^6$, $R^7$, $R^8$, $R^9$, and $R^{11}$ each independently represent a hydrogen atom, a cyano group, a halogen atom, or an unsubstituted aliphatic hydrocarbon group having 1 to 20 carbon atoms, and $R^{10}$ is a nitro group; and (B) a photosensitive resin.

6. The photosensitive resin composition according to claim 5, wherein $R^1$ in general formula (1) is a substituted or unsubstituted phenyl group.

7. A cured product obtained by irradiating the photosensitive resin composition according to claim 5 with energy rays.

* * * * *